(12) United States Patent
Khan et al.

(10) Patent No.: US 12,250,992 B2
(45) Date of Patent: Mar. 18, 2025

(54) DATA-ANALYZING SMART INSOLE APPARATUS AND METHOD

(71) Applicant: LAAF, Inc., Wilmington, DE (US)

(72) Inventors: Meher Khan, Wilmington, DE (US); Zain Hussain, Wilmington, DE (US); Faasel Khan, Wilmington, DE (US)

(73) Assignee: LAAF, Inc., Wilmington, DE (US)

( * ) Notice: Subject to any disclaimer, the term of this patent is extended or adjusted under 35 U.S.C. 154(b) by 0 days.

(21) Appl. No.: 18/263,529

(22) PCT Filed: Feb. 15, 2022

(86) PCT No.: PCT/US2022/070669
§ 371 (c)(1),
(2) Date: Jul. 29, 2023

(87) PCT Pub. No.: WO2022/183166
PCT Pub. Date: Sep. 1, 2022

(65) Prior Publication Data
US 2024/0090620 A1 Mar. 21, 2024

Related U.S. Application Data

(60) Provisional application No. 63/154,252, filed on Feb. 26, 2021.

(51) Int. Cl.
*G08B 13/14* (2006.01)
*A43B 3/40* (2022.01)
(Continued)

(52) U.S. Cl.
CPC ............ *A43B 17/00* (2013.01); *A43B 3/40* (2022.01); *A43B 3/44* (2022.01); *A43B 3/48* (2022.01);
(Continued)

(58) Field of Classification Search
CPC .. A43B 17/00; A43B 3/40; A43B 3/44; A43B 3/48; A61B 5/1038; A61B 5/112;
(Continued)

(56) References Cited

U.S. PATENT DOCUMENTS 7,969,315 B1 6/2011 Ross et al.
2015/0313308 A1 11/2015 Rice et al.
(Continued)

FOREIGN PATENT DOCUMENTS

KR 20180065161 A 6/2018
WO 2016167401 A1 10/2016

OTHER PUBLICATIONS

American Podiatric Medical Association. Jan. 2009. (8 pages) https://www.apma.org/files/FileDownloads/APMAFootAilments-SurveyNewsWorthyAnalysis012309.pdf.
(Continued)

*Primary Examiner* — Tai T Nguyen
(74) *Attorney, Agent, or Firm* — MUGHAL GAUDRY & FRANKLIN PC

(57) ABSTRACT

Smart insoles provide comfort and support while analyzing gait, improving posture and alignment, and tracking fitness metrics. Raw data from the smart insoles is fed into normative data algorithms to create a unique user report in real-time. A mobile app associated with the smart insole connects users to caregivers, articles, and personalized exercises. Monitoring of these parameters is used for managing chronic pain and sedentary lifestyle. The smart insole is a smart wearable device with a mobile app to monitor and manage chronic pain, which is an effective strategy in reducing foot pain and increasing physical activity.

14 Claims, 10 Drawing Sheets

(51) Int. Cl.
| | |
|---|---|
| A43B 3/44 | (2022.01) |
| A43B 3/48 | (2022.01) |
| A43B 17/00 | (2006.01) |
| A61B 5/00 | (2006.01) |
| A61B 5/103 | (2006.01) |
| A61B 5/11 | (2006.01) |

(52) U.S. Cl.
 CPC ............ *A61B 5/1038* (2013.01); *A61B 5/112* (2013.01); *A61B 5/6807* (2013.01); *A61B 2562/0247* (2013.01)

(58) Field of Classification Search
 CPC .......... A61B 5/6807; A61B 2562/0247; A61B 5/7225; A61B 2560/0223
 USPC ...................................................... 340/573.1
 See application file for complete search history.

(56) References Cited

U.S. PATENT DOCUMENTS

| | | | |
|---|---|---|---|
| 2016/0093199 A1 | 3/2016 | Whitney et al. | |
| 2016/0299021 A1* | 10/2016 | Thillainadarajah | ..... G01L 5/169 |
| 2018/0054663 A1* | 2/2018 | Markison | ............ A61B 5/1118 |
| 2018/0085030 A1* | 3/2018 | Krimmer | ............ A43B 17/006 |
| 2018/0256071 A1* | 9/2018 | Mathieu | ............... A61B 5/1036 |
| 2021/0368925 A1* | 12/2021 | Schneider | ............ A43B 13/023 |
| 2022/0099504 A1* | 3/2022 | Yuan | .................... H10N 30/045 |
| 2022/0395229 A1* | 12/2022 | Everett | ................. G08B 21/02 |

OTHER PUBLICATIONS

Blair et al., "Physical Fitness and All-Cause Mortality. A Prospective Study of Healthy Men and Women," in JAMA. Nov. 1989; 3:262(17):2395-401.doi: 10.1001/jama.262.17.2395.

Carlson et al., "Percentage of Deaths Associated with Inadequate Physical Activity in the United States," in Prev Chronic Dis. Mar. 29, 2018;15:E38. doi: 10.5888/pcd18.170354.

Franklin et al., "Cardiorespiratory Fitness: An Independent and Additive Marker of Risk Stratification and Health Outcomes," in Mayo Clin Proc. Sep. 2009; 84(9): 776-779 (4 pages).https://pubmed.ncbi.nlm.nih.gov/3945246/.

Global Action Plan on Physical Activity 2018-2030 (104 pages)chrome-extension://efaidnbmnnnibpcajpcglclefindmkaj/https://apps.who.int/iris/bitstream/handle/10665/272722/9789241514187-eng.pdf?sequence=1&isAllowed=y.

Holmes, "Feet Are Getting Bigger, and Many People Wear Shoes That Don't Fit Right," in The Wall Street Journal, 2014.

International Search Report & Written Opinion notified May 26, 2022 for PCT Patent Application No. PCT/US2022/070669.

Kim et al., "Chronic Pain, Physical Activity, and All-Cause Mortality in the US Adults: The NHANES 1999-2004 Follow-Up-Study," in Am J Health Promot. Nov. 2019. 33(8):1182-1186. doi: 10.1177/0890117119854041.

Kohl 3rd et al., "The Pandemic of Physical Inactivity: Global Action for Public Health," in Lancet Jul. 21, 2012. 380 (9838):294-305. doi: 10.1016/S0140-6736(12)60898-8.

Lee et al., "Real-World Use and Self-Reported Health Outcomes of a Patient-Designed Do-it-Yourself Mobile Technology System for Diabetes: Lessons for Mobile Health," in Diabetes Technol Ther. Apr. 2017;19(4):209-219. doi: 10.1089/dia.2016.0312.

Lin et al., "Smart insole: A Wearable Sensor Device for Unobtrusive Gait Monitoring in Daily Life," in IEEE Transactions on Industrial Informatics, vol. 12, No. 6. pages 2281-2291, Dec. 2016.doi: 10.1109/TII.2016.2585643.

McKay et al., "1000 Norms Project: Protocol of a Cross-Sectional Study Cataloging Human Variation," in Physiotherapy2016 Mar; 102(1):50-6. doi: 10.1016/j.physio.2014.12.002.

Mickle et al., "The Feet of Overweight and Obese Young Children: are they flat or fat?," in Obesity (Silver Spring) Nov. 2006; 14(11):1949-53. doi: 10.1038/oby.2006.227.

Paffenbarger et al., "Physical Activity, All-Cause Mortality, and Longevity of College Alumni," in New Engl J Med. Mar. 6, 1986. 314(10):605-12. doi: 10.1056/NEJM198603063141003.

Physical Inactivity a Leading Cause of Disease and Disability. (2 pages). downloaded on Jul. 25, 2023.https://www.who.int/news/item/04-04-2002-physical-inactivity-a-leading-cause-of-disease-and-disability-warns-whoi.

Saidani et al., "A Survey on Smart Shoe Insole Systems," 2018 International Conference on Smart Communications and Networking (SmartNets), Yasmine Hammamet, Tunisia, 2018, pp. 1-6.doi: 10.1109/SMARTNETS.2018.8707391.

Schoenborn et al., "Health Behaviors of Adults: United States, 2005-2007," in Vital Health Stat 10., Mar. 2010; (245): 1-132 (143 pages).

Volkow et al., "Opioid Abuse in Chronic Pain—Misconceptions and Mitigation Strategies," in N Engl J Med Mar. 31, 2016; 374:1253-1263DOI: 10.1056/NEJMra1507771.

\* cited by examiner

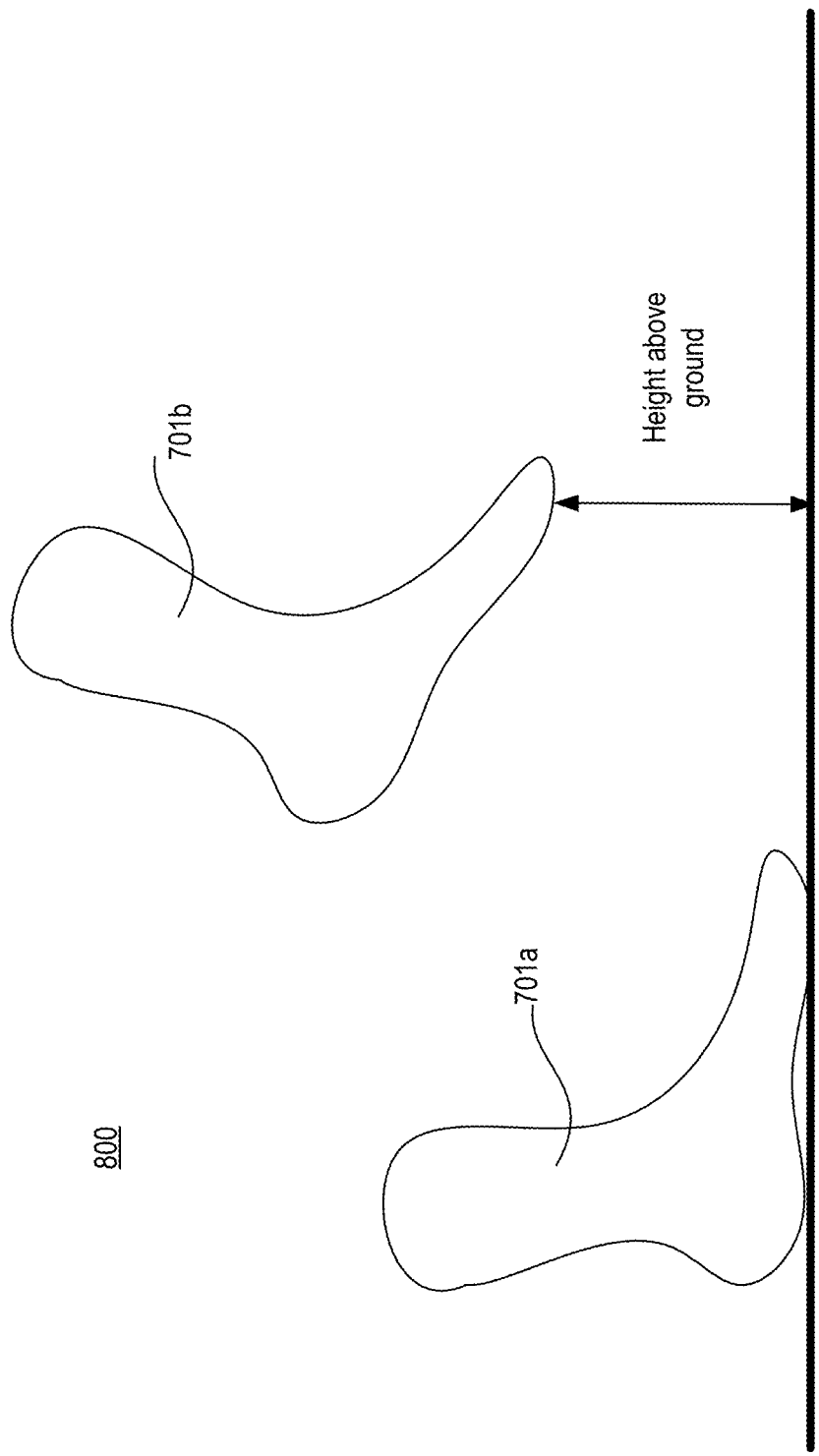

DATA-ANALYZING SMART INSOLE APPARATUS AND METHOD

CLAIM OF PRIORITY

This application is a National Stage application of, and claims the benefit of priority to International Patent Application No. PCT/US2022/070669, filed Feb. 15, 2022, which claims the benefit of priority to U.S. Provisional Patent Application 63/154,252, filed on Feb. 26, 2021, titled "DATA-ANALYZING SMART INSOLE APPARATUS AND METHOD," and which are incorporated by reference in its entirety.

BACKGROUND

About 80% of Americans experience foot pain each year, with about 40% suffering from heel pain. Flat footed adults in the United States (US) make up about 8% of the total US population (18 million people). Physical inactivity is increasing in the US, and it is one of the leading causes of preventable deaths accounting for approximately 365,000 (15.2%) deaths, in the year 2000. The percentage of US adults who regularly engage in the recommended amount of leisure-time exercise is estimated at approximately 30.7%. Researchers predict that the combined effect of physical inactivity and poor nutrition will soon surpass smoking as the leading cause of preventable death if obesity rates continue to rise. Worldwide, 1 in 4 adults, and 3 in 4 adolescents (aged 11-17 years) do not meet the physical activity standards set by the World Health Organization (WHO). Physical inactivity is a significant risk factor in obese and overweight diabetics at 24% in Pakistan. By the age of 80, the amount of additional life attributable to exercise, as compared to sedentariness can be more than two years. Higher levels of physical fitness lead to improved health outcomes. A study in the United Kingdom (UK) found that a third of men and a half of the women surveyed have admitted to wearing shoes that do not fit. Some of the most common reasons for foot pain are poorly-fitting shoes (unsupportive), standing for long hours (overuse), and displaced foot pressures (misalignment). Feet alignment varies over time with changes in weight, age, pregnancy, or chronic disease. The consequences for mal-alignment include common foot ailments, such as bunions, blisters, hammertoes, neuropathy, and improper gait.

Improper gait is not easily visible. However, the effects of improper gait can impact the entire lower body, not just the foot. Improper gait affects the kinetic chain of the body, which is the interconnected checkpoints in the body responsible for movement from the feet and ankles through the legs and knees to the hips and even the lower back. Existing solutions improperly address the unique alignment in each foot, access to quality care and evidence-based information. This may lead to over-reliance on painkillers and self-medication.

Chronic lower body pain is a pervasive problem in the US and globally. People with flat feet are more likely to experience plantar fasciitis, Achilles tendonitis, calluses, corns, blisters, bunions, hammertoes, shin splints, among many other ailments. If untreated, these issues may develop into more serious injuries and chronic pain. Physical inactivity due to chronic pain predisposes one to a cluster of metabolic diseases. Management and prevention of chronic foot pain using current standards of care methods remains a challenge.

The background description provided here is for the purpose of generally presenting the context of the disclosure. Unless otherwise indicated here, the material described in this section is not prior art to the claims in this application and are not admitted being prior art by inclusion in this section.

BRIEF DESCRIPTION OF THE DRAWINGS

The embodiments of the disclosure will be understood more fully from the detailed description given below and from the accompanying drawings of various embodiments of the disclosure, which, however, should not be taken to limit the disclosure to the specific embodiments, but are for explanation and understanding only.

FIG. 8 illustrates a view of human legs with smart insole above ground in swing phase, in accordance with some embodiments.

DETAILED DESCRIPTION

Figure 1:
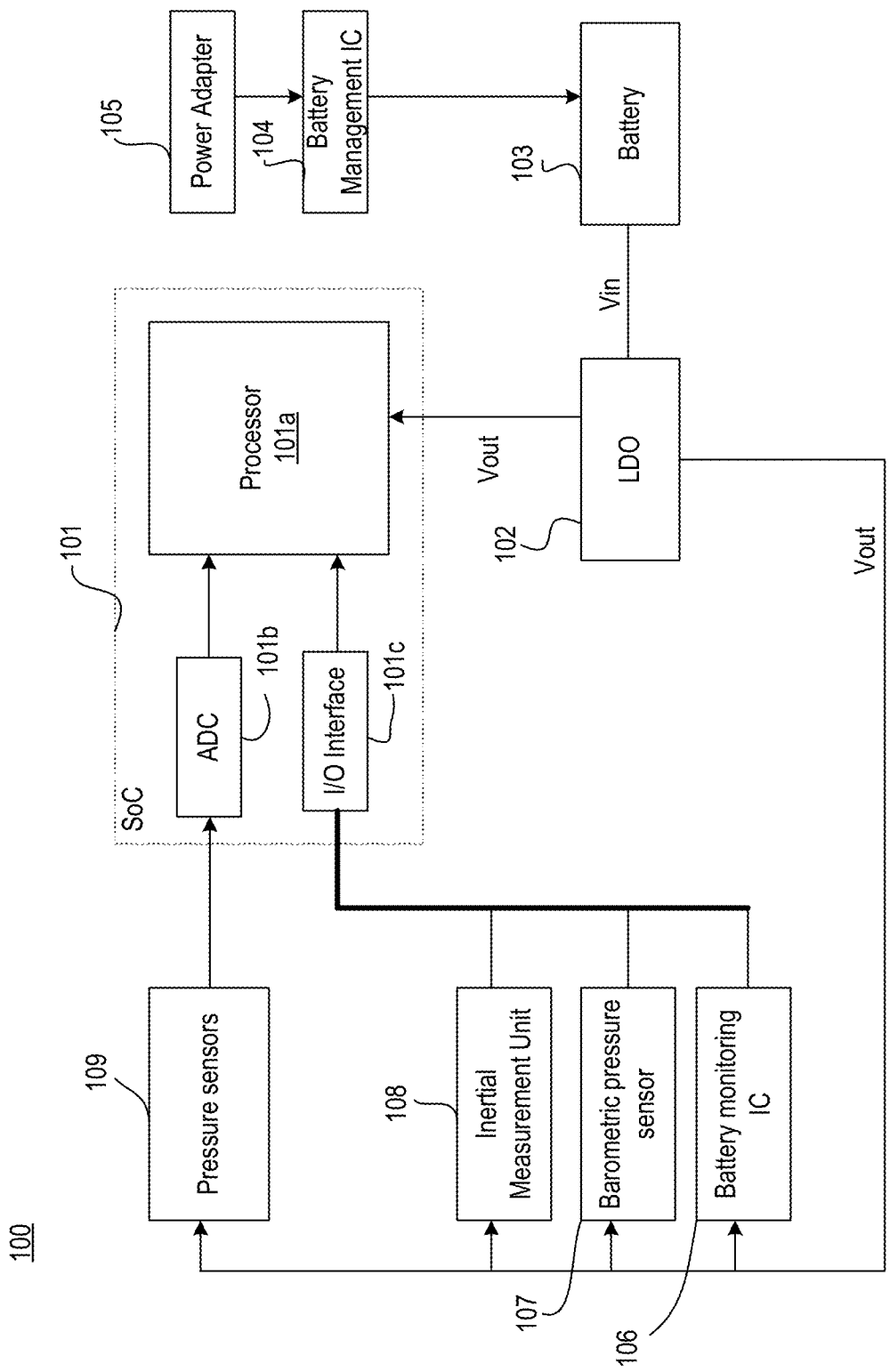
FIG. 1 illustrates a system of various electronic components in the smart insole, in accordance with some embodiments.

Gait and movement abnormalities can be identified, and users can be coached to improve their posture, cadence, and alignment based on their unique data. Smart insoles can be used to help sufferers avoid injuries in the form of calcaneus fractures, Lisfranc dislocations, chronic plantar fasciitis, chronic lower back pain and worsening knee osteoarthritis. Implanting sensors in the insoles can help one identify, through walking patterns, development of some of the aforementioned disorders and recovery progression via machine learning. There is much room for integrated research in studying the remedial effects of using smart insoles with inbuilt sensors, barometers, and inertial measurement units.

Various embodiments address the role of physical activity in reducing mortality risk for individuals with chronic pain by enabling a healthy and active lifestyle via a data-analyzing smart insole. The insole (also referred to as a footwear insole apparatus) of some embodiments provides comfort and support while analyzing gait, improving posture and alignment, and tracking fitness metrics. Raw data from the smart insoles is fed into normative data algorithms to create a unique user report in real-time. Some embodiments provide a mobile application (app) associated with the smart insole. The mobile application (app) connects users to caregivers, articles, and personalized exercises. Monitoring of these parameters provides the management of chronic pain and sedentary lifestyle. Some embodiments that use a smart wearable device with a mobile app to monitor and manage chronic pain would be an effective strategy in reducing foot pain and increasing physical activity.

Various sensors and components of some embodiments are embedded in the insole. In some embodiments, users may opt to receive a signal on their mobile app when their parameters are in an abnormal range for self-management. In some embodiments, raw data is analyzed via deep learning algorithms to provide personalized recommendations, access to state-of-the-art literature, blogs, and connections to expert caregivers all on a mobile app for comprehensive management. In some embodiments, in-person or remote telehealth appointments can be booked with licensed providers, high-rated personal trainers, physiotherapists, and foot specialists using the map feature in the mobile app or on a website or portal associated with the smart insole.

In some embodiments, accurate performance of each sensor, barometer, and Inertial Management Unit (IMU) data with complete performance metrics, heat maps, graphs, and pain scale are evaluated via a communication interface (e.g., Bluetooth low energy) to a mobile application as a comprehensive tool to manage chronic pain. Mobile health studies indicate that using mobile health to monitor chronic disease with mutual feedback between users and caregivers, leads to improved health outcomes. Other technical effects will be evidence from the various figures and embodiments.

In the following description, numerous details are discussed to provide a more thorough explanation of embodiments of the present disclosure. It will be apparent, however, to one skilled in the art, that embodiments of the present disclosure may be practiced without these specific details. In other instances, well-known structures and devices are shown in block diagram form, rather than in detail, to avoid obscuring embodiments of the present disclosure.

Note that in the corresponding drawings of the embodiments, signals are represented with lines. Some lines may be thicker, to indicate more constituent signal paths, and/or have arrows at one or more ends, to indicate primary information flow direction. Such indications are not intended to be limiting. Rather, the lines are used in connection with one or more exemplary embodiments to facilitate easier understanding of a circuit or a logical unit. Any represented signal, as dictated by design needs or preferences, may actually comprise one or more signals that may travel in either direction and may be implemented with any suitable type of signal scheme.

Throughout the specification, and in the claims, the term "connected" means a direct connection, such as electrical, mechanical, or magnetic connection between the things that are connected, without any intermediary devices.

Here, the term "analog signal" is any continuous signal for which the time varying feature (variable) of the signal is a representation of some other time varying quantity, i.e., analogous to another time varying signal.

Here, the term "digital signal" is a physical signal that is a representation of a sequence of discrete values (a quantified discrete-time signal), for example of an arbitrary bit stream, or of a digitized (sampled and analog-to-digital converted) analog signal.

The term "coupled" means a direct or indirect connection, such as a direct electrical, mechanical, or magnetic connection between the things that are connected or an indirect connection, through one or more passive or active intermediary devices.

The term "adjacent" here generally refers to a position of a thing being next to (e.g., immediately next to or close to with one or more things between them) or adjoining another thing (e.g., abutting it).

The term "circuit" or "module" may refer to one or more passive and/or active components that are arranged to cooperate with one another to provide a desired function.

The term "signal" may refer to at least one current signal, voltage signal, power signal, magnetic signal, or data/clock signal. The meaning of "a," "an," and "the" include plural references. The meaning of "in" includes "in" and "on."

The terms "substantially," "close," "approximately," "near," and "about," generally refer to being within +/−10% of a target value.

Unless otherwise specified, the use of the ordinal adjectives "first," "second," and "third," etc., to describe a common object, merely indicate that different instances of like objects are being referred to and are not intended to imply that the objects so described must be in a given sequence, either temporally, spatially, in ranking or in any other manner.

For the purposes of the present disclosure, phrases "A and/or B" and "A or B" mean (A), (B), or (A and B). For the purposes of the present disclosure, the phrase "A, B, and/or C" means (A), (B), (C), (A and B), (A and C), (B and C), or (A, B and C).

The terms "left," "right," "front," "back," "top," "bottom," "over," "under," and the like in the description and in the claims, if any, are used for descriptive purposes and not necessarily for describing permanent relative positions.

It is pointed out that those elements of the figures having the same reference numbers (or names) as the elements of any other figure can operate or function in any manner similar to that described but are not limited to such.

FIG. 1 illustrates system 100 of various electronic components in the smart insole, in accordance with some embodiments. System 100 includes system-on-chip (SoC) 101 (or processor 101), voltage regulator 102, battery 103, battery management integrated circuit (IC) 104, power adaptor 105 (also referred to as charging connector), battery monitoring IC 106, barometric pressure sensor 107, inertial measurement unit 108, and pressure sensors 109. In some embodiments, SoC 101 includes processor 101a, analog-to-digital converter (ADC) 101b, and input-output (I/O) interface 101c.

In some embodiments, processor 101a is a Digital Signal Processor (DSP), an Application Specific Integrated Circuit (ASIC), or a general-purpose Central Processing Unit (CPU). Processor 101 can have a single core or multiple processor cores. In some embodiments, processor 101a is coupled to a communication interface for wirelessly communicating data to another device. Such a device may be a smart phone, a server, a cloud, etc. In some embodiments, processor 101a is an ARM based Nordic processor (e.g., BMD 350) with standalone Bluetooth module (e.g., Bluetooth 5.0 module) which connects a mobile application and sends/receives data parameters to and from the mobile application.

In some embodiments, ADC 101b is an apparatus that converts continuous physical quantities (e.g., voltages) to digital numbers that represent the amplitude of the physical quantities. In some embodiments, ADC 101b converts the analog output of pressure sensors 109 to their corresponding digital representations. Any suitable ADC may be used to implement ADC 101b. For example, ADC 101b is one of: direct-conversion ADC (for flash ADC), two-step flash ADC, successive-approximation ADC (SAR ADC), ramp-compare ADC, Wilkinson ADC, integrating ADC, delta-encoded ADC or counter-ramp, pipeline ADC (also called sub-ranging quantizer), sigma-delta ADC (also known as a delta-sigma ADC), time-interleaved ADC, ADC with intermediate FM stage, or time-stretch ADC. For purposes of explaining the various embodiments, ADC 101*b* is 7-bit a flash ADC.

In some embodiments, I/O interface 101*c* interfaces with a plurality of sensors such as battery monitoring IC 106, barometric pressure sensor 107, and inertial measurement unit 108. Information from these sensors is provided to processor 101*a*. In some embodiments, I/O interface 101*c* is a I2C interface.

In some embodiments, the various components of system 100 are powered by voltage regulator 102. Voltage regulator 102 can be any suitable regulator. Examples of such a regulator include low dropout (LDO) regulator, DC-DC converter, etc. An example of the LDO is a TLV702 device by Texas Instruments Inc. In various embodiments, voltage regulator 102 receives an input voltage Vin on an input supply line and provides a regulated output voltage Vout on an output supply line. In some embodiments, voltage regulator 102 converts input voltage to 3.3 Volts for providing regulated power to the processor and sensors. In some embodiments, the input voltage Vin (and its associated current) is provided by battery 103.

In some embodiments, battery 103 comprises any suitable battery such as a Lithium-ion (Li-ion) battery, a coin battery, a rechargeable battery, etc. In one example, battery 103 is a single cell battery that provides 3.5 V and 300 mAh. In some embodiments, battery 103 is controlled by battery management IC 104. In some embodiments, battery management IC monitors adaptor voltage to ensure optimal charging of battery 103. In some embodiments, battery management IC 103 may control the amount of charging current to battery 103.

In some embodiments, power adaptor 105 provides an external power source to charge battery 103. In some embodiments, power adaptor 105 is a Universal Serial Bus (USB) based adaptor. Examples of USB based adaptor are USB 2.0 Type-B, USB Type-C and other similar adaptors. The embodiments are not limited to USB adaptors. Other types of adaptors may also be used.

In some embodiments, a plurality of sensors (e.g., sensors 106, 107, 108, and 109) are powered by LDO 102. In some embodiments, battery monitoring IC 106 comprises one or more sensors to monitor the health of battery 103. For example, battery monitoring IC 106 acts like a fuel gauge and provides telemetry information such as current voltage, load current, temperature, rate of change in voltage on Vout, rate of change in current on the supply line Vout, battery charge level, change in battery charge level, etc. of battery 103. This telemetry information is provided to processor via I/O interface 101*c*, in accordance with some embodiments. In some embodiments, processor 101*a* computes the battery charge level or rate of degradation of battery 103 using the telemetry information. In some embodiments, processor 101*a* may change performance (e.g., output voltage on Vout) by instructing battery monitoring IC 106 to adjust a reference voltage for LDO 102.

In some embodiments, barometric pressure sensor 107 is provided which provides data for calculating height of foot above the ground while walking. This data is provided to processor 101*a* via I/O interface 101*c*. In some embodiments, this information is used to determine user movement behavior and gait. In some embodiments, inertial measurement unit 108 is provided which provides data for calculating parameters related to time, speed, and angles associated with the insoles. In some embodiments, inertial measurement unit 108 is a 6-axis inertial measurement device. In some embodiments, the insoles include pressure sensors 109 that provide point pressure and resistance data for the heat map. The heat map is formed by the pressure of the foot on the insole. In some embodiments, the insole has multiple pressure sensors 109. For example, the insole has seven 0.6-inch force sensitive resistor (FSR) based sensors that behave as pressure sensors 109.

In various embodiments, the smart insole collects gait cycle data, which is analyzed in the mobile application, which is communicatively coupled to processor 101*a*. This data is presented for a complete analysis of cadence, pronation, supination, acceleration, balance, and pressure on each foot with changes compared to baselines and normative data. Users can opt to receive alerts when these parameters exceed defined thresholds. With these reports, the mobile app may connect users to personalized solutions to address the root causes of their pain, and access exercises, blogs, and articles, as well as schedule appointments with local caregivers specialized in lower body pain.

Smart insoles can offer precise acquisition of running biomechanics from both feet, while comfortably providing an unobtrusive way to monitor, providing a full analysis of a person's performance and running technique. Furthermore, a smartphone Android and/or iOS mobile app displays sensor data in real-time via Bluetooth low energy. In various embodiments, the smart insoles can be easily paired through Bluetooth to the mobile device. Once connected, one can see, in real-time, a heat map, distance, time, elevation, gait cycle, cadence, step length, foot strike, and pronation/supination displayed on the main home screen of the application. By simply tapping on each metric, the user is provided with additional insights and suggestions for performance adjustments. Another great feature is the Caregiver Appointment booking directly through the application. Caregivers and users can have a live session by having the user wear an insole and record the real time values at the time of appointment for a defined period of time. Data collection by these appointments can be very insightful, as it can help the caregiver determine the prescription orthotics and optimal exercises. An online store, also located in the application, makes it easy to find the correct pair of high-quality insoles and other items at reasonable prices.

Some embodiments use force sensitive resistors to measure pressure denoted by a colored heat map; and a barometer and 6-axis inertial measurement unit (IMU) to calculate gait parameters like angle of elevation, pronation/supination, cadence, and height above the ground. The smart insoles of some embodiments are designed to study the body mechanics of the user for a healthy lifestyle. The insole can calculate the important parameters for dynamic postures during various activities, as required by caregivers. Deep learning and machine learning techniques are applied in these parameters to recommend suitable exercises for the treatment of chronic foot pain.

To monitor the pressure, in one example, seven anatomical sites are considered including first, second and fourth-fifth metatarsal heads, talonavicular joint and calcaneocuboid joint and heel. In some embodiments, the sensor placement also coincides with sciatic nerve, lumbar, knee and hip joint areas on a reflexology map. The mobile app can monitor pressure heat maps, and complete analysis of cadence, pronation, supination, heel-toe walkers, acceleration and stoppage time, balance, and pressure on each foot with change of direction as compared to baseline and normative data. If any of these parameters exceed a defined range, the application provides patients warnings to make changes confirmed by caregivers. Consequently, this device by providing real-time foot monitoring and deep learning algorithmic analysis, empowers users for comprehensive management to reduce pain, prevent further injuries and maintain physical activity levels. Internal validation shows the accurate performance of pressure sensors to recognize the maximum pressures on the foot for all participants with IMU transmitted metrics to the mobile app in real time with defined timed reports.

With the smart insoles and mobile app, active users may see reduction in their pain levels. In-App interaction between caregivers and users may assist caregivers to remotely access reports and assess progress over time. Those suffering from heel pain, plantar fasciitis, bunions, or hammertoes can feel relief with the comfort of the insole, while also working towards a proactive solution that addresses the underlying problems. Users recovering from previous injuries can use the mobile app to monitor their progress in rehabilitation. This level of integration between collected data and real-time feedback allows the user to adjust with minimal effort. The smart insoles provide a comprehensive solution to the root causes of pain.

The connected strategy of various embodiments provides a continuous low friction solution with telehealth, personalized reports via deep learning data algorithms, curated exercises, and peer-to-peer and blog functionality, all in one app. Precise deep learning of raw continuous data into relevant recommendations by the app assists clinicians to recognize patterns and use predictions to guide their practice and can significantly improve health outcomes. Whether it starts from an injury or from overuse and lack of support, pain can lead to reduced physical activity and over-reliance on pain medication. The smart insole and app of various embodiments guides users through their healthcare journeys as they learn more about their underlying cause of pain and find experienced caregivers to assist them. The unique approach of recommending solutions and providing a central repository for pain management allows users to find the best solutions with minimal time spent on irrelevant and imprecise research.

Figure 2:
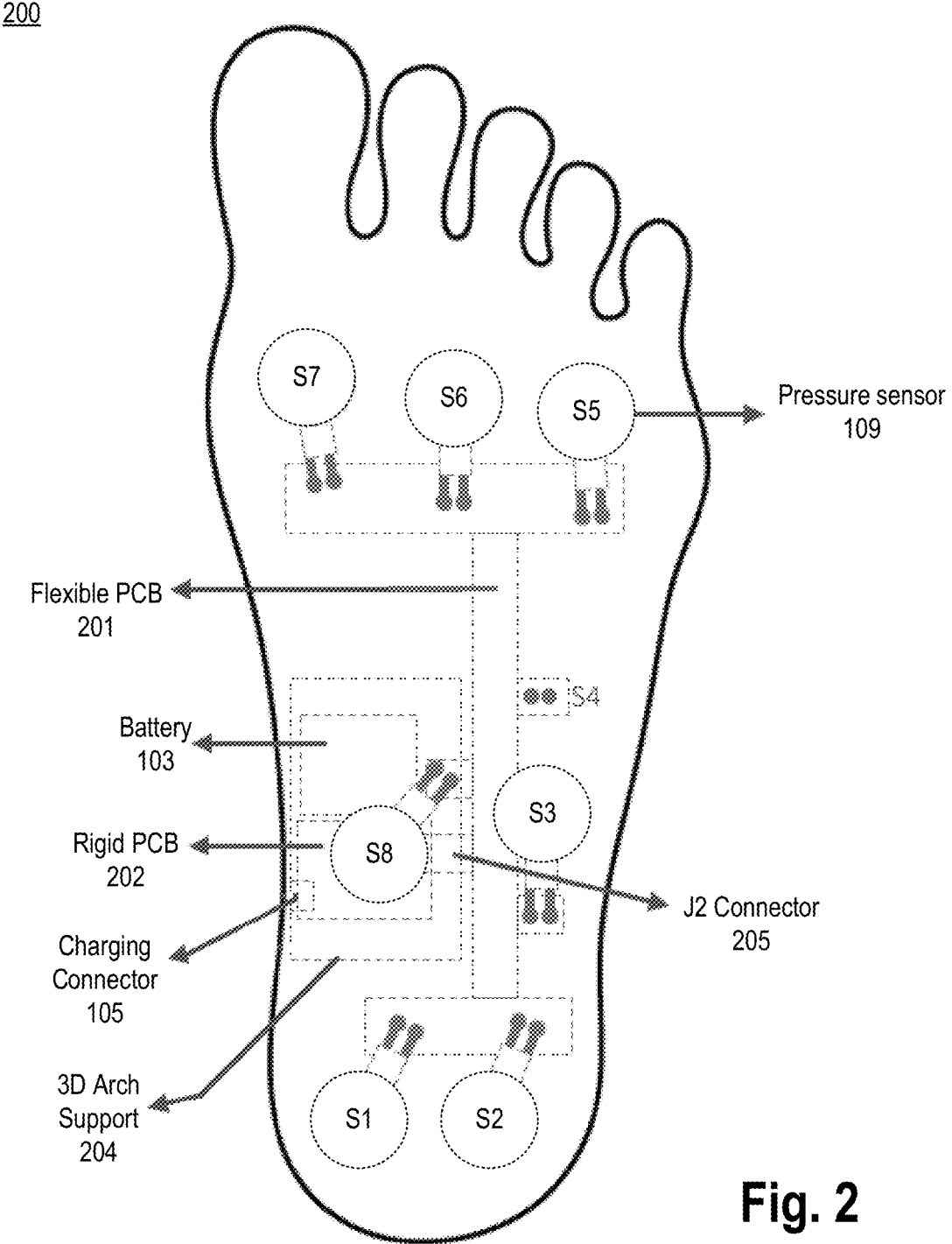
FIG. 2 illustrates a cross-sectional view of the smart insole with placement of various sensors, in accordance with some embodiments.

FIG. 2 illustrates a cross-sectional view 200 of smart insole with placement of various sensors, in accordance with some embodiments. In various embodiments, the smart insole comprises an elongated flexible material which houses the apparatus described with reference to FIG. 1. In some embodiments, the smart insole comprises flexible printed circuit board (flexible PCB) 201. In some embodiments, the smart insole comprises PCB 202. In some embodiments, the smart insole comprises foot arch support structure 204, battery 103, power adaptor 105, connector 205, pressure sensors 109 and/or other components of FIG. 1. In some examples, flexible PCB has a bending ratio of 1%. In some embodiments, PCB 202 is a relatively rigid PCB compared to flexible PCB 201.

Here, flexible PCB refers to a PCB with material that allows the PCB to bend with a bending ratio of 1%-5%. Conversely, a rigid PCB is not flexible and has a bending ratio of 0-0.5%. In some examples, a flexible PCB has more layers than a rigid PCB. In one instance, a rigid PCB has 5 or more layers while a flexible PCB 202 has fewer than 5 layers. Flexible PCB 202 can be bent to fit into small spaces or follow the curves of any shape it is being place on or inside. In some embodiments, during manufacturing of the PCB, a hard copper plate is used in rigid PCBs and in case of flexible PCB the copper plate is foldable and is made of either copper or electrolytic copper.

In this exemplary embodiment, seven pressure sensors 109 (labeled as S1 through S7) are distributed or placed in different sections of the smart insole with the help of flexible PCB 201. As such, point pressure is measured at various locations of the insole to measure the pressure of the foot along its contours and pressure areas. Different areas of the insole (due to shape of the foot) sense different levels of forces. In some embodiments, pressure sensors 109 are of the same sensitivity. In some embodiments, depending on the sensitive part of the foot, sensitive pressure sensors may be used to measure the foot pressure. These force variations from pressure sensors 109, along with other parameters from barometric sensor 107 and inertial measurement unit (IMU) 108, are processed and analyzed within the microcontroller 101 (or SoC 101) placed on rigid PCB 202. By placing SoC 101 on rigid PCB 202 allows for maintaining the physical integrity of the SoC 101 and its components. In some embodiments, SoC 101 includes capability of communicating with another device. For example, SoC 101 may use Bluetooth for communication. Using Bluetooth, microcontroller 101 sends data processed by microcontroller 101 to an application (e.g., an application being executed on a mobile device, cloud computer, or any other computing device). While the embodiments show seven sensors, fewer or more sensors can be added and placed in the insole to collect more data.

In some embodiments, the complete circuitry of the smart insole is powered by using a single cell Lithium-Ion battery 103 (e.g., 3.7V/400 mAh). To check how much percentage battery 103 is charged, rigid PCB 202 uses battery monitoring IC 104 on board. Battery monitoring IC 104 (e.g., fuel gauge) may be attached to the microcontroller I2C bus (or any suitable interconnect) and helps to monitor the instantaneous or real time voltages of battery 103, which is then converted into a percentage. In case the charge level of battery 103 is low, a user can charge the insole by using charging connector 105 such as a USB B type cable (or any other suitable interface such as USB Type-C, Thunderbolt, etc.). In one example, the charging connector 105 (or power adaptor) has a 5V/0.5 A rating. In some embodiments, battery management IC 104 has a built-in over-voltage protection support that helps charge battery 103 with extra security in three different stages of conditioning, constant current, and constant voltage.

Figure 3:
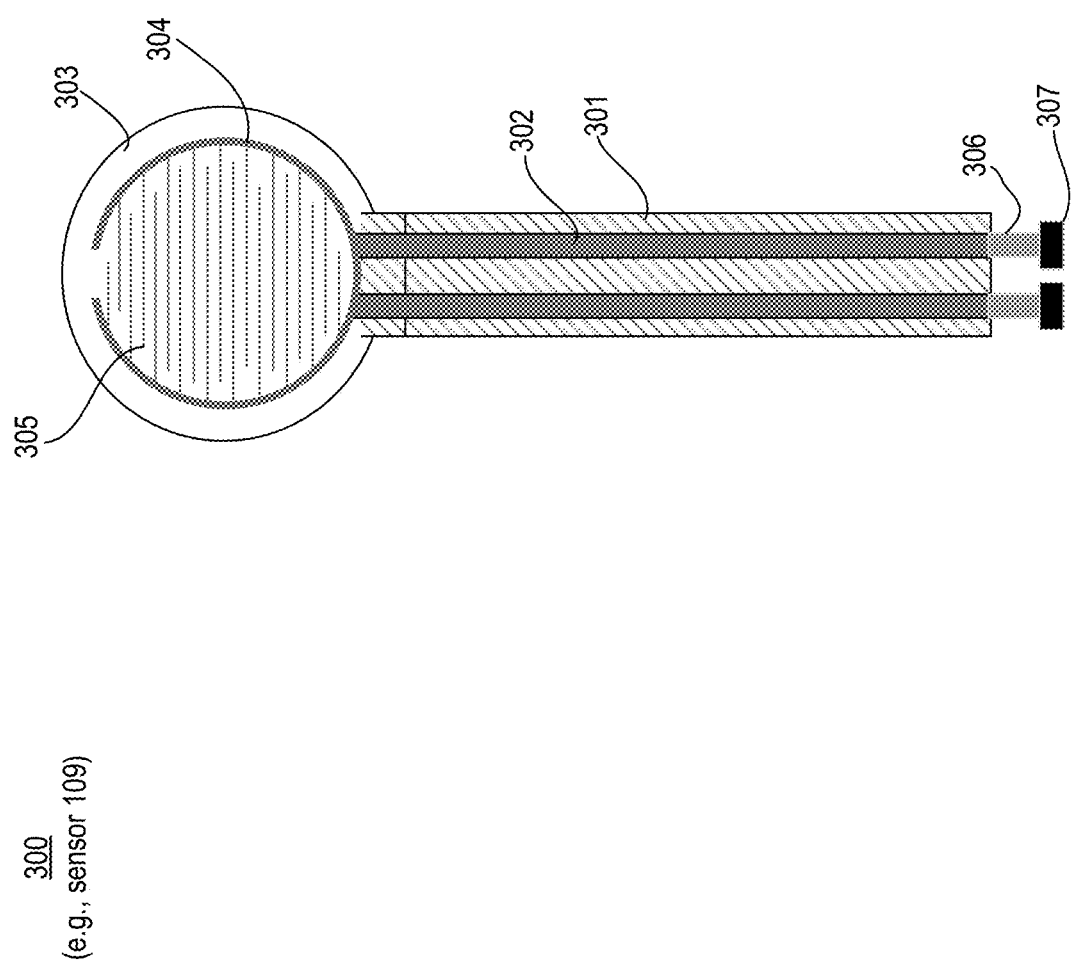
FIG. 3 illustrates a force sensitive sensor (FSR) for the smart insole, in accordance with some embodiments.

FIG. 3 illustrates a force sensitive sensor (FSR) 300 (e.g., sensor 109) for the smart insole, in accordance with some embodiments. One of the parameters in gait analysis is the pressure distribution along the foot. There are multiple sensors used in literature and available in the market that are used to calculate the force applied to a certain area, such as Ceramic Piezoelectric Sensors, Micro-Electromechanical Systems (MEMS) Sensors, and Force-Sensitive Resistor (FSR) Sensors. To make a system effective, simple to use, and cost efficient, FSR sensor is used as illustrated in FIG. 3.

In some embodiments, sensor 300 comprises flexible substrate 301, conductor 302 on or within substrate 301, spacer material 303, circular conductor portion 304 with a conductive mesh 305, conducting terminals 306, and contacts 307. Sensor 300 is used to calculate the pressure applied to conductive mesh 305 (e.g., 0.5-inch sensitive bit area). Sensor 305 acts as the variable resistor whose resistance varies according to the pressure on it. This change in resistance is detected at contacts 307. If the pressure increases, then the resistance of sensor 300 goes down and vice versa. If there is no pressure on sensor 300, then the resistance becomes infinite and sensor 300 acts as an open circuit. Similarly, if the pressure is less, the resistance becomes approximately, for example, 100 kΩ (kilo-ohms), and if there is a maximum pressure on the sensor, then it drops down to a minimum resistance up to, for example, 200Ω (ohms).

Figure 4:
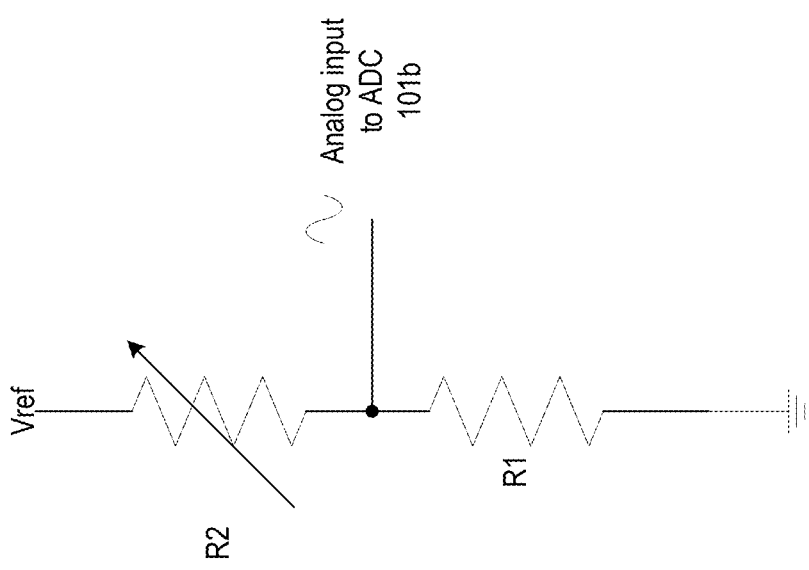
FIG. 4 illustrates an FSR as a pull-down resistor for the smart insole, in accordance with some embodiments.

FIG. 4 illustrates FSR 400 (e.g., model of FSR 300) as a pull-down resistor R1 for the smart insole, in accordance with some embodiments. The FSR sensors are used as a pull-down resistor to give input to the pins of ADC 101b of SoC 101 for processing to calculate the pressure variations. In some embodiments, the sensitivity of sensor 400 is controlled by resistor R2 which is in series with resistor R1 and also connected to a reference voltage Vref. Any suitable circuit may be used for generating the reference voltage Vref. For example, a resistor divider, a bandgap circuit etc. can be used to generated Vref. In some embodiments, resistance of R2 is adjustable or programmable by enabling or disabling resistors in parallel. As such, the overall pressure sensitivity of FSR 400 can be modified or adjusted, in accordance with some embodiments.

Figure 5:
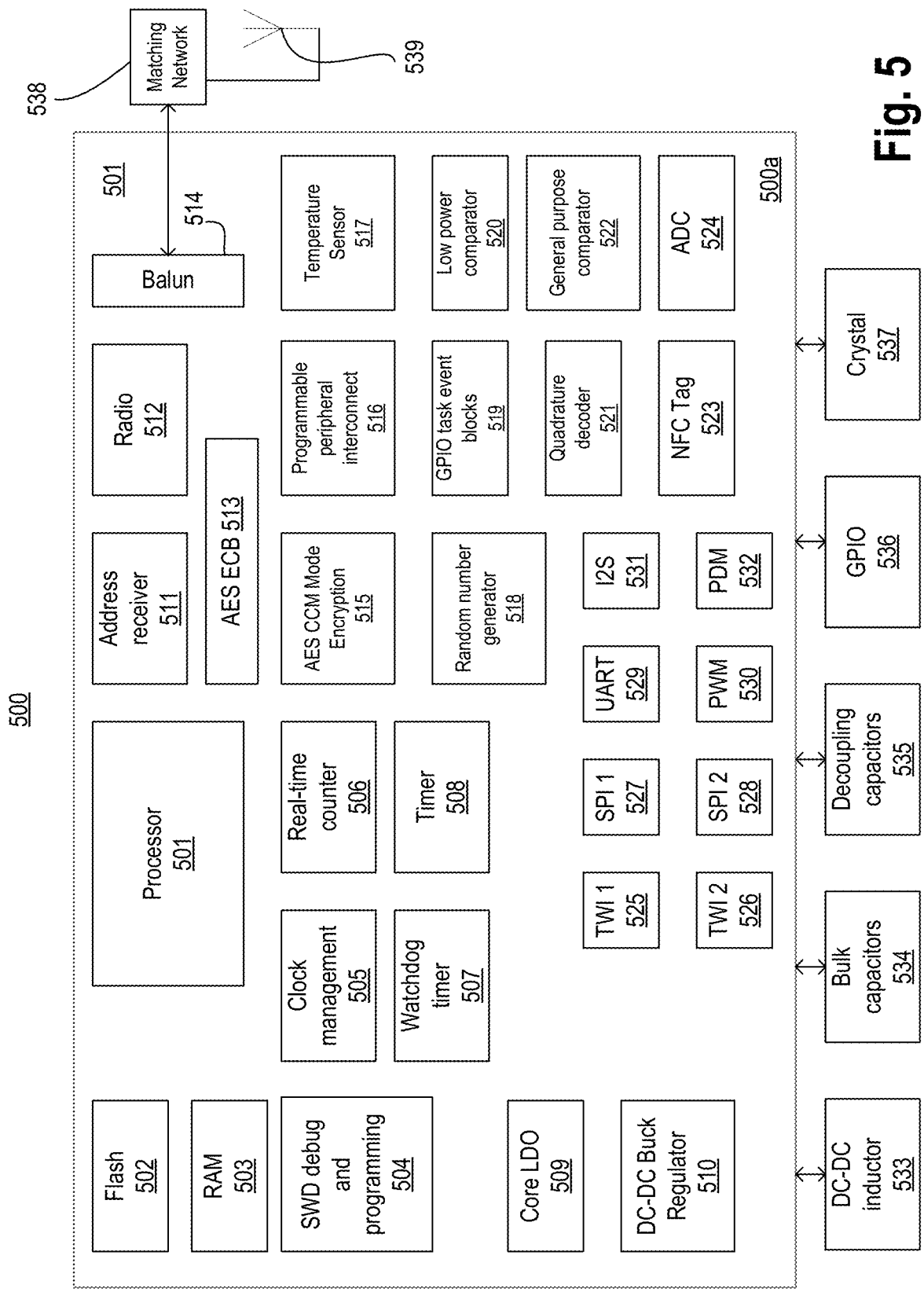
FIG. 5 illustrates a high-level diagram of a system-on-chip (SoC) for the smart insole, in accordance with some embodiments.

FIG. 5 illustrates a high-level diagram of a system-on-chip (SoC) 500 (e.g., 101) or microcontroller for the smart insole, in accordance with some embodiments. In one example, SoC 500 is based on a U-Blox BMD-350 A R Module. The U-Blox BMD 350 A R module is based on Nordic Semiconductor's NRF52832. However, other SoC or microcontrollers may be used in the smart insole to sense and analyze data and communicate with a mobile application. In some embodiments, SoC 500 includes a processor block 500a comprising processor 501, non-volatile flash memory 502, random access memory (RAM) 503, software (SWD) debug and programming logic 504, clock management circuitry 505, real-time counter 506, watchdog timer 507, timer 508, core low-dropout (LDO) regulator 509, DC-DC buck regulator 510, address receiver 511, radio 512, Advanced Encryption Standard (AES) electronic codebook mode encryption (ECB) 513, Balun 514, AES cipher block chaining message authentication code (CCM) 515, programmable peripheral interconnect 516, temperature sensor 517, random number generator 518, general purpose IP (GPIO) task even blocks 519, low power comparator 520, quadrature decoder 521, general purpose comparator 522, near field communication (NFC) tag 523, ADC 524, first two-wire interface (TWI 1) 525, second two-wire interface (TWI 2) 526, first serial peripheral interface (SPI 1) 527, second serial peripheral interface (SPI 2) 528, universal asynchronous transmitter receiver (UART) 529, pulse width modulator (PWM) 530, inter-IC sound (I2S) interface 531, and power distribution module (PDM) 532. In various embodiments, processor block 500a is coupled to DC-DC inductor 533, bulk capacitors 534, decoupling capacitors 535, GPIO 536, crystal oscillator 537, antenna matching network 538, and antenna 539.

In some embodiments, ultra-low-power Bluetooth low energy module can establish communication from multiple peripherals and center point at a time and provide better control over the quality and bandwidth of the transmitting and receiving signal. The module can be a 32-bit microprocessor that means it can process 32 bits of data per clock cycle. The module can further have 512 kb flash, and 64 kb RAM to store and process the application code. Besides this, there are other useful built-in features that can be used in different customized applications.

Figure 6:
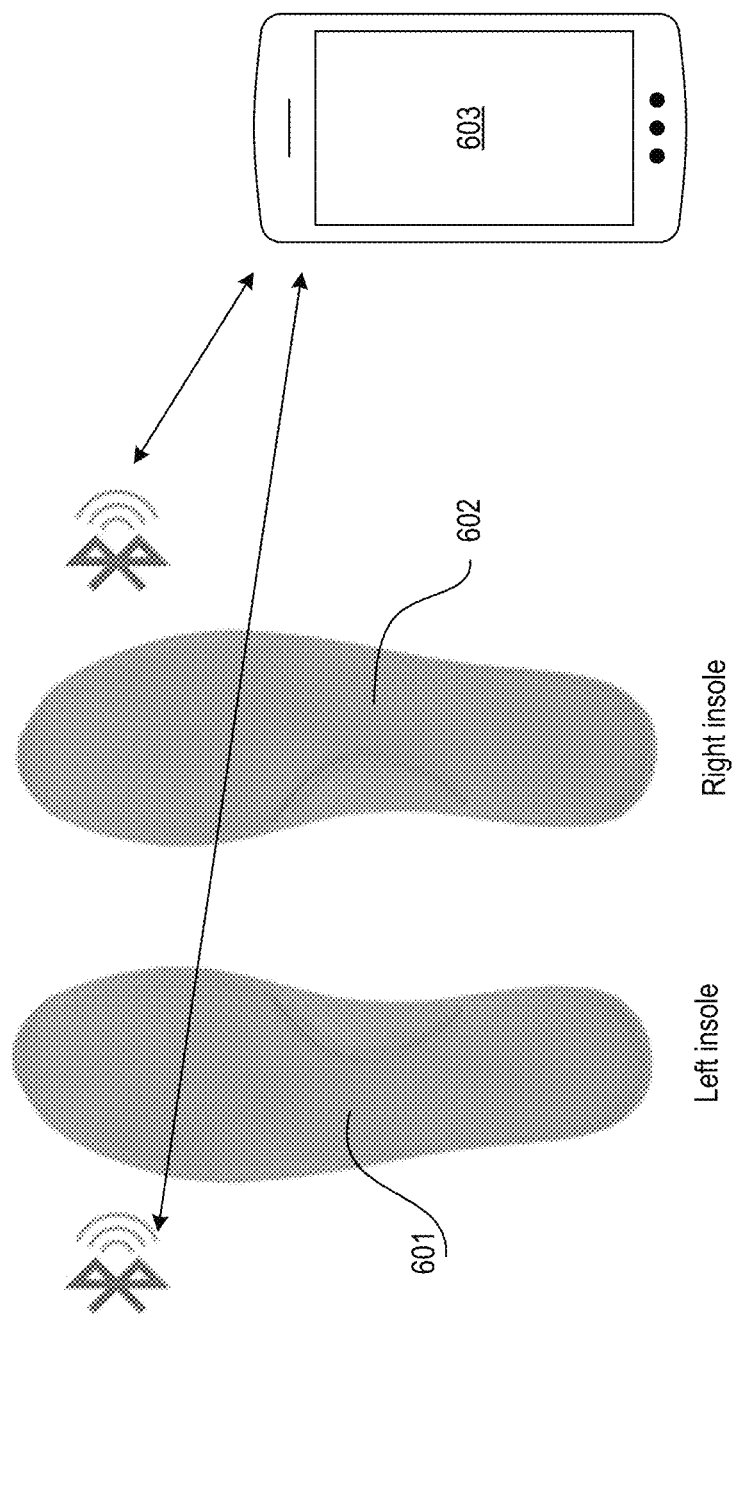
FIG. 6 illustrates a smart insole ecosystem with a mobile device in communication with the smart insole, in accordance with some embodiments.

FIG. 6 illustrates smart insole ecosystem 600 with a mobile device in communication with the smart insole, in accordance with some embodiments. Ecosystem 600 comprises a pair of insoles 601 and 602, and a mobile or computing device 603 with an application executing on it. Data from multiple sensors of the smart insole are processed within microcontroller 101 and transmitted to an application end of device 603 via high-speed transmission, e.g., 5.2 Bluetooth signals, for the treatment of a user. For communication, both the insoles 601 and 602 act as peripherals that can send data from the user end to the application end, which is the central unit, in accordance with some embodiments. In some embodiments, the raw data from microcontroller 101 in insoles 601 and 602 is analyzed via deep learning (or any other machine-learning technique) and curated to each unique user on its way to the central unit. Later, caregivers can use this data from the insoles that are received in the application end for management strategies.

Figure 7:
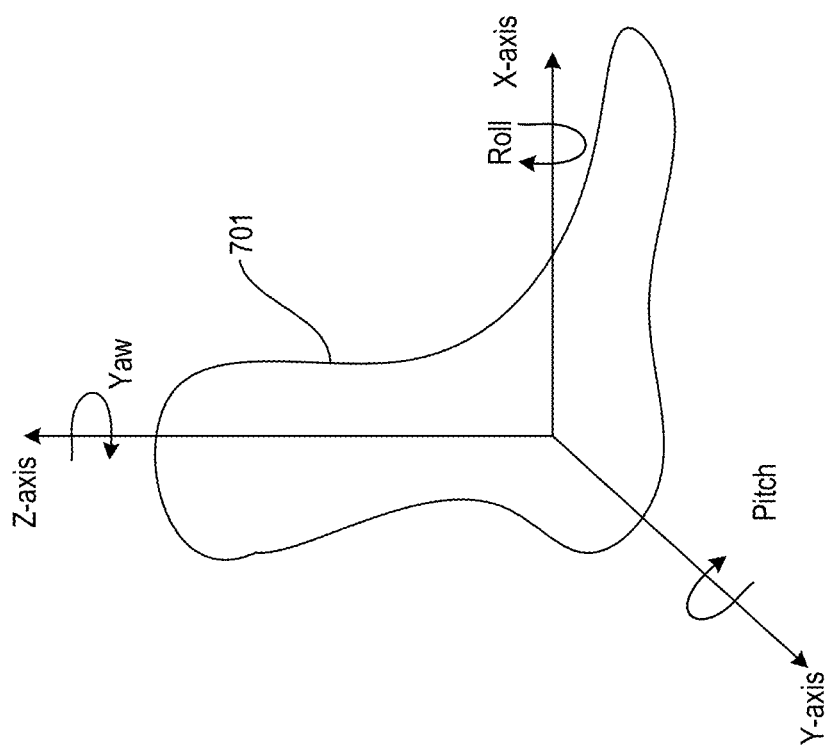
FIG. 7 illustrates a view of a foot with roll, pitch, and yaw angles for the right foot.

FIG. 7 illustrates view 700 of a foot with roll, pitch, and Yaw angles for the right foot. To calculate the motion-related parameters of foot 701, the 6-axis inertial measurement unit (IMU) 108 is used within the insole that comprises one or more 3-Axis accelerometer(s) and one or more 3-axis gyroscope(s). With the help of the acceleration and gyroscope readings along X, Y, and Z axes, the roll, pitch, and yaw values are calculated that change in degrees. These roll, pitch, and yaw values are important to calculate the gait parameters like angle of elevation, pronation/supination, and progression. In some embodiments, IMU 108 interacts with the microcontroller and other sensors with the help of I2C bus.

FIG. 8 illustrates view 800 of human feet 701a and 701b with smart insole above ground in swing phase, in accordance with some embodiments. In some embodiments, barometric sensor 107 is used to measure the atmospheric pressure at a certain height and it is attached to the I2C bus 101c of microcontroller 101. The atmospheric pressure reading changes according to the distance above or below the sea level. For another gait analysis parameter, this pressure data is transformed into height above ground and is calculated within the swing phase as shown in FIG. 8, in accordance with some embodiments.

Table 1 illustrates a list of gait parameters calculated from the various sensors used by the smart insole, in accordance with some embodiments.

TABLE 1

| No. | Parameters | Pressure sensor | Inertial Measurement Unit | | Barometer pressure sensor | Battery Monitoring IC |
|---|---|---|---|---|---|---|
| | | | Accelerometer | Gyroscope | | |
| 1 | Angle of elevation (heel strike) | yes | yes | yes | | |
| 2 | Angle of pronation/supination (Heel strike) | yes | yes | yes | | |
| 3 | Angle of elevation (Mid stance) | yes | yes | yes | | |

TABLE 1-continued

| No. | Parameters | Pressure sensor | Inertial Measurement Unit Accelerometer | Gyroscope | Barometer pressure sensor | Battery Monitoring IC |
|---|---|---|---|---|---|---|
| 4 | Angle of pronation/supination (Mid Stance) | yes | yes | yes | | |
| 5 | Angle of elevation (Toe Off) | yes | yes | yes | | |
| 6 | Angle of pronation/supination (Toe Off) | yes | yes | yes | | |
| 7 | Angle of progression | yes | yes | yes | | |
| 8 | Mid stance time | yes | | | | |
| 9 | Heel strike time | yes | | | | |
| 10 | Toe off time | yes | | | | |
| 11 | Time swing | yes | | | | |
| 12 | Stride length | yes | yes | | | |
| 13 | Average stride length | yes | yes | | | |
| 14 | Gait cycle time | yes | | | | |
| 15 | cadence | yes | | | | |
| 16 | speed | yes | yes | | | |
| 17 | steps | yes | yes | | | |
| 18 | Battery level | | | | | yes |
| 19 | Step clearance | yes | | | | |
| 20 | Height above ground | yes | | | yes | |
| 21 | Distance covered | yes | yes | | | |

Figure 9A:
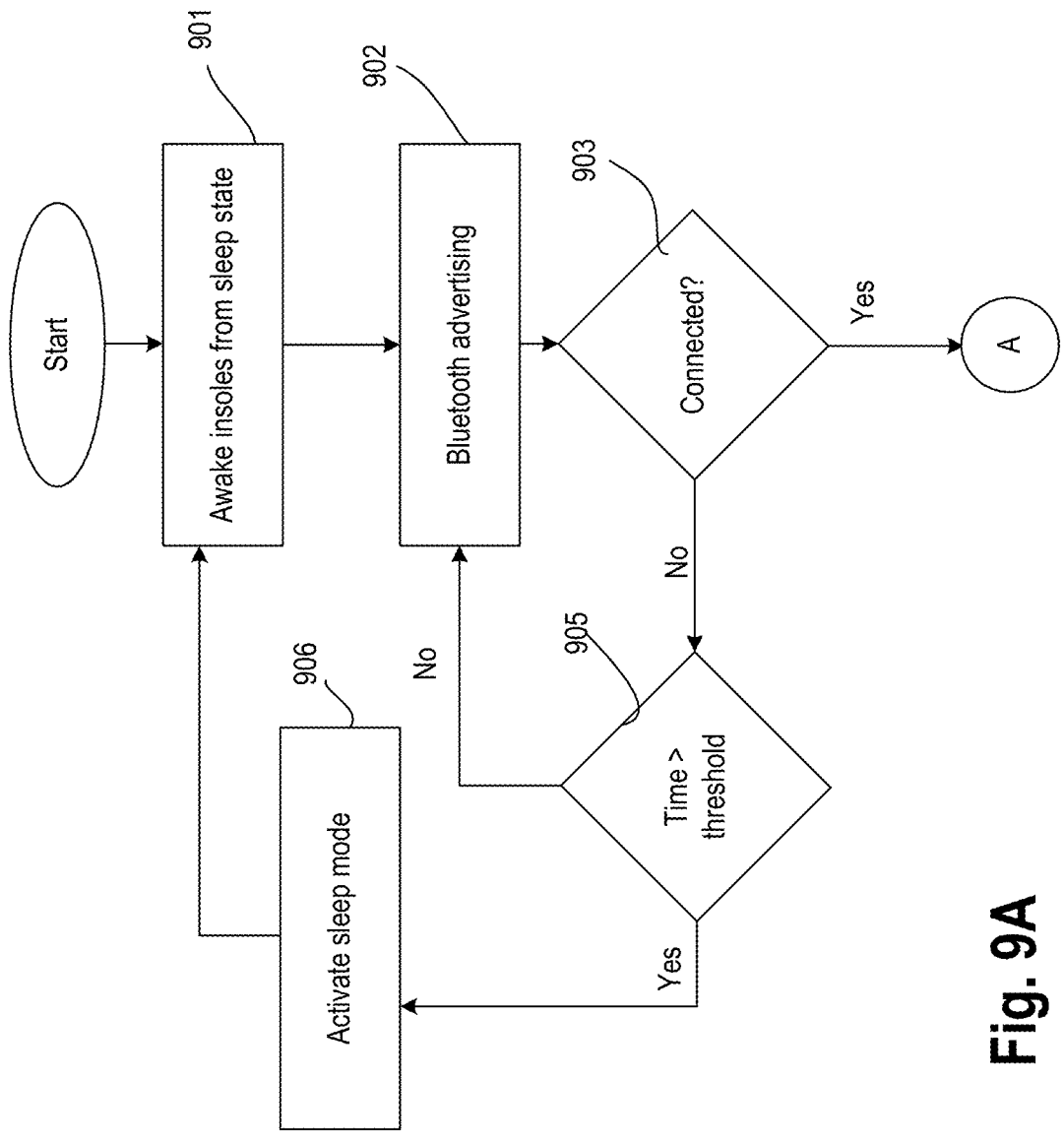
FIGS. 9A-B illustrate a flowchart of method of operating the smart insole, in accordance with some embodiments.
Figure 9B:
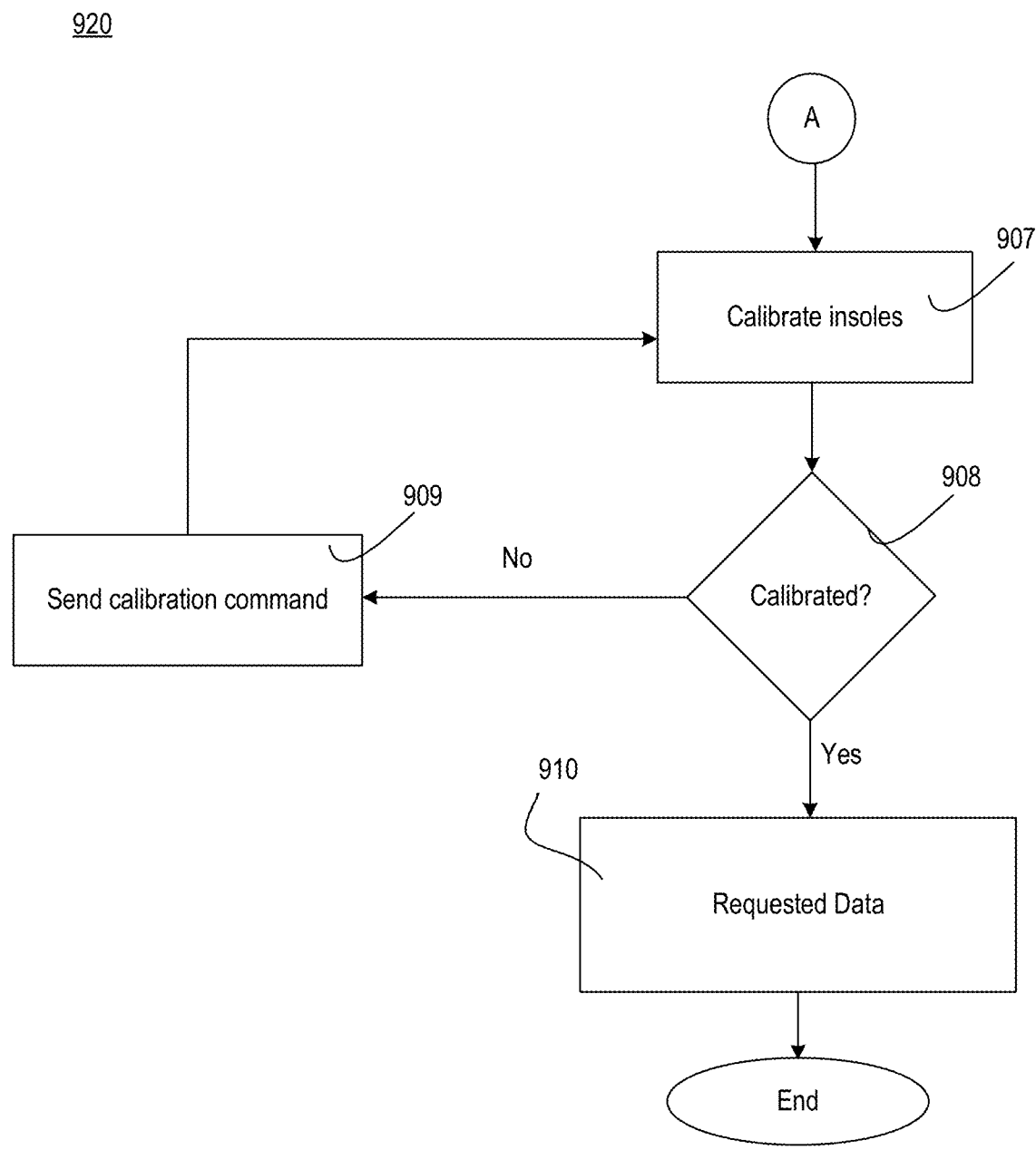

FIGS. 9A-B illustrate flowcharts 900 and 920, respectively, of method of operating the smart insole, in accordance with some embodiments. While various blocks in the flowchart are shown in a particular order, the order can be modified. For example, some blocks can be performed before others while some blocks may be performed in parallel. The blocks in the flowchart can be implemented by software, hardware, or a combination of them.

Upon powering on the insole or stepping into the shoe having the insole, at block 901, the insoles are awakened from their sleep state (e.g., deep sleep state). In some embodiments, microcontroller 101 is transitioned from a sleep state or low power state to operational or active state at block 901. In some embodiments, a power management block in microcontroller 101 or external to microprocessor 101 instructs LDO 102 to provide the power on Vout power supply rail to power on microcontroller 101 and other sensors or components in the insoles. Insoles are wearable devices where power consumption is considered as a factor of long-term operation. In some embodiments, deep sleep mode is a useful feature that helps to save maximum power whenever there is no activity recording for a long time. For example, if the insoles are not in use, then the system enters in system off mode and turns off all its peripherals except the midfoot sensors. Whenever the user needs to wake the insole from the deep sleep mode, he/she just needs to exert some pressure on the surface of the insole.

At block 902, microcontroller 101 begins or initiates the process of pairing the separate insoles with one another and/or with an external device (e.g., a mobile phone, a computer, etc.). This process is referred to as Bluetooth advertising and may be initiated in response to waking up the system from the low power state. Before connecting to the application (e.g., mobile app), the insoles advertise itself with a unique Bluetooth name (Left/Right Insole) and an identifier (e.g., a 16-bit long service Universally Unique Identifier (UUID)). These attributes help to establish the proper connection or communication channel between the peripheral (insoles) and central point (application), in accordance with some embodiments. While the embodiments are illustrated with reference to Bluetooth connectivity, any other similar technology may be used to pair or establish networking connection between the insoles and the application (e.g., software) or computing device (e.g., hardware).

At block 903, microcontroller 101 determines whether the insole(s) are connected with the application or computing device. If the connection is successful, the process proceeds to block 907 as indicated by identifier A. If the microcontroller 101 determines whether the insole(s) are not connected with the application or computing device, then microcontroller 101 may check at block 905 if the duration to connect has lapsed. For example, at block 905, microcontroller 101 determines whether a time window to connect or establish a Bluetooth connection between the insole and the application (or device) has expired. This time window can be a programmable threshold or a fixed threshold time. If the time to establish the connection passes a threshold, then the process proceeds to block 906. For example, if no connection is established in the given time window or threshold time, then it may be that the insoles are not in use and so microcontroller 101 puts itself and other devices associated with it into sleep mode or low power mode. Any known power management schedule or technique may be used to place microcontroller 101 and/or its associated devices (e.g., sensors) in low power mode. For example, power gating, clock gating, modulation of power supply Vout, throttling of clock frequency, etc. may be used to lower the power of the insoles in low power mode.

In some embodiments, if no connection is established in the given time window or threshold time, then microcontroller 101 may give another chance for the insole to connect. As such, the process may proceed to block 902 where Bluetooth advertising is redone. In some examples, the time to establish a connection (e.g., the threshold time) is about 1 minute. This time can be programmable by software, hardware, or a combination of them.

At block 907, after a successful communication connection, microcontroller 101 calibrates the insoles. This calibration is applied as the same insole pair can be used in multiple different shoes. For example, the same insoles may be used for varying sole thickness and to cater for this change, when the smart insole is turned on, the smart insole runs an automatic calibration cycle. In some embodiments, the calibration processor can be triggered or executed manually or by pressing a button available on the application (App) end. If, while the smart insole is on and connected to the application (App), the user changes the shoe, it may be advised to manually recall the calibration process otherwise faulty parameter readings may be observed. Insoles comprise flexible material that conforms to the shape of the lower outer surface of the foot. In some embodiments, calibration of the insoles happens before data is transferred by microcontroller 101 to a mobile app. Before calculating the gait parameters, the calibration redefines the origin of the IMU gyroscope and accelerometer axis.

In some embodiments, when the insole pair gets successfully connected with the Application, an automated command may be sent from the application end to the controller. On receiving the command, the controller may send out a command to IMU 108 and requests for updated offset values of accelerometer and gyroscope. These offset values are calculated within IMU 108 as per the manufacturing system and are sent back to the controller, in accordance with some embodiments. In some embodiments, the offset values are updated in a string which is further utilized to calculate various parameters based on the IMU data. In some embodiments, an acknowledgement is sent to the App, confirming the completion of the calibration cycle.

At block 908, microcontroller 101 determines whether the calibration process completed successfully. For example, microcontroller 101 checks whether the insoles are providing error free measurements or not. If there are errors in calibration, or errors are not removed, microcontroller 101 issues a calibration command as indicated by block 909. In some embodiments, a user of a mobile application receives a notice or alert that the calibration did not complete successfully and/or there were errors in the calibration. If the insoles are not calibrated and providing false data, then a user can simply press a button given in the application to calibrate insoles again, in accordance with some embodiments. If there are no errors after calibration and all sensors are working as expected, the insoles are ready to calculate gait parameters. Upon calculating the gait parameters, microcontroller 101 sends the requested data of the sensors to the application as indicated by block 910.

In some embodiments, the application (e.g., mobile app) receives all the measurements from the insoles and processes it. In some embodiments, there are two types of data transmitted from insoles. One is real time data, and the other is average data. In some embodiments, the real time data provides gait parameters of each step immediately without any delay while the average data provides average gait parameters over a selected time span. In some embodiments, the requested data sent by microcontroller 101 to the mobile app includes force variations, heel strike data (e.g., elevation, pronation, supination, heel strike time, etc.), mid stance data (e.g., elevation, pronation, supination, mid stance time, etc.), toe-off data (e.g., elevation, pronation, supination, toe-off time), angle of progression, stride length, gait cycle, cadence, speed, steps taken, distance covered, step clearance, height above ground, and/or battery status. In some embodiments, some or all the requested data may be reconfigured in a report and sent to a media professional as a message regarding the user's insole parameters.

Elements of embodiments are also provided as a machine-readable medium (e.g., memory) for storing the computer-executable instructions (e.g., instructions to implement any other processes discussed herein). In some embodiments, a computing platform comprises a memory, a processor, a machine-readable storage media (also referred to as tangible machine-readable medium), a communication interface (e.g., wireless or wired interface), and a network bus coupling them.

In some embodiments, processor 101 comprises a Digital Signal Processor (DSP), an Application Specific Integrated Circuit (ASIC), a general-purpose Central Processing Unit (CPU), or a low power logic implementing a simple finite state machine to perform the method of various embodiments, etc.

In some embodiments, the various logic blocks of system 100 are coupled together via the network bus. Any suitable protocol may be used to implement the network bus. In some embodiments, the machine-readable storage medium includes instructions (also referred to as the program software code/instructions) stored thereon for processing the sensor data as described with reference to the various embodiments and flowchart. The machine-readable storage medium may be part of processor 101 or external to processor 101. The machine-readable storage medium may comprise volatile or non-volatile memory.

Program software code/instructions associated with flowchart(s) (and/or various embodiments) and executed to implement embodiments of the disclosed subject matter may be implemented as part of an operating system or a specific application, component, program, object, module, routine, or other sequence of instructions or organization of sequences of instructions referred to as "program software code/instructions," "operating system program software code/instructions," "application program software code/instructions," or simply "software," or firmware embedded in the processor. In some embodiments, the program software code/instructions associated with flowcharts (and/or various embodiments) are executed by the computer system.

In some embodiments, the program software code/instructions associated with flowcharts (and/or various embodiments) are stored in a computer executable storage medium and executed by the processor. Here, computer executable storage medium is a tangible machine-readable medium that can be used to store program software code/instructions and data that, when executed by a computing device, causes one or more processors to perform a method(s) as may be recited in one or more accompanying claims directed to the disclosed subject matter.

The tangible machine-readable medium may include storage of the executable software program code/instructions and data in various tangible locations, including for example ROM, volatile RAM, non-volatile memory and/or cache and/or other tangible memory as referenced in the present application. Portions of this program software code/instructions and/or data may be stored in any one of these storage and memory devices. Further, the program software code/instructions can be obtained from other storage, including, e.g., through centralized servers or peer to peer networks and the like, including the Internet. Different portions of the software program code/instructions and data can be obtained at different times and in different communication sessions or in the same communication session.

The software program code or instructions (associated with flowcharts 900 and 920 and other embodiments) and data can be obtained in their entirety prior to the execution of a respective software program or application by the computing device. Alternatively, portions of the software program code/instructions and data can be obtained dynamically, e.g., just in time, when needed for execution. Alternatively, some combination of these ways of obtaining the software program code/instructions and data may occur, e.g., for different applications, components, programs, objects, modules, routines or other sequences of instructions or organization of sequences of instructions, by way of example. Thus, it is not required that the data and instructions be on a tangible machine-readable medium in entirety at a particular instance of time.

Examples of tangible computer-readable media include but are not limited to recordable and non-recordable type media such as volatile and non-volatile memory devices, read=only memory (ROM), random access memory (RAM), flash memory devices, magnetic random-access memory, ferroelectric memory, floppy and other removable disks, magnetic storage media, and optical storage media (e.g., Compact Disk Read-Only Memory (CD ROMS), Digital Versatile Disks (DVDs), etc.), among others. The software program code/instructions may be temporarily stored in digital tangible communication links while implementing electrical, optical, acoustical, or other forms of propagating signals, such as carrier waves, infrared signals, digital signals, etc. through such tangible communication links.

In general, the tangible machine-readable medium includes any tangible mechanism that provides (i.e., stores and/or transmits in digital form, e.g., data packets) information in a form accessible by a machine (i.e., a computing device), which may be included, e.g., in a communication device, a computing device, a network device, a personal digital assistant, a manufacturing tool, a mobile communication device, whether or not able to download and run applications and subsidized applications from the communication network, such as the Internet, e.g., an iPhone®, Galaxy®, Blackberry® Android®, or the like, or any other device including a computing device. In one embodiment, processor-based system is in a form of or included within a PDA (personal digital assistant), a cellular phone, a notebook computer, a tablet, a game console, a set top box, an embedded system, a TV (television), a personal desktop computer, etc. Alternatively, the traditional communication applications and subsidized application(s) may be used in some embodiments of the disclosed subject matter.

In various embodiments, the machine-readable media and processor to execute the instruction in the machine-readable media are part of the mobile or computing device described herein.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may," "might," or "could" be included, that particular component, feature, structure, or characteristic is not required to be included. If the specification or claim refers to "a" or "an" element, that does not mean there is only one of the elements. If the specification or claims refer to "an additional" element, that does not preclude there being more than one of the additional elements.

Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive.

The following examples presented as claims pertain to further embodiments. Specifics in the examples may be used anywhere in one or more embodiments. All optional features of the apparatus described herein may also be implemented with respect to a method or process.

Example 1: A footwear insole apparatus comprising: a flexible printed circuit board; a relatively rigid printed circuit board coupled to the flexible printed circuit board; a plurality of pressure sensors coupled to the flexible printed circuit board; and a processor coupled to the relatively rigid printed circuit board, wherein the processor is to receive sensor data from the plurality of pressure sensors.

Example 2: The footwear insole apparatus of example 1, comprising a battery coupled to the relatively rigid printed circuit board, wherein the battery is used to power the plurality of pressure sensors and the processor.

Example 3: The footwear insole apparatus of example 2, comprising a battery monitoring integrated circuit coupled to the processor via an I/O interface, wherein the battery monitoring integrated circuit is to provide a first data to calculate a charge level of the battery.

Example 4: The footwear insole apparatus of example 3, comprising an inertial measurement unit coupled to the processor via the I/O interface, wherein the inertial measurement unit is to provide a second data to calculate parameters related to time, speed, and angles of the footwear insole apparatus.

Example 5: The footwear insole apparatus of example 3, comprising barometric sensor coupled to the processor via the I/O interface, wherein the barometric sensor is to provide a third data to calculate height of the footwear insole apparatus above a ground.

Example 6: The footwear insole apparatus of example 1, comprising an analog-to-digital converter (ADC) to receive an analog data from the plurality of pressure sensors and to generate a corresponding digital data for the processor.

Example 7: The footwear insole apparatus of example 2, comprising a voltage regulator to receive an input supply from the battery and to generate an output supply for the plurality of pressure sensors and the processor.

Example 8: The footwear insole apparatus of example 1, wherein the processor is to establish a Bluetooth connection with another device.

Example 9: The footwear insole apparatus of example 1, wherein the processor is to calibrate one or more sensors prior to transfer of data to another device.

Example 10: The footwear insole apparatus of example 1, wherein the processor is to enter a lower power mode if there is no pressure detected by the plurality of pressure sensors.

Example 11: A machine-readable storage media having machine-readable instructions stored thereon that, when executed, cause one or more machines to perform a method comprising: waking up, one or more sensors and a processor, from a low power mode in response to detection that an insole is in use; initiating advertisement for communication with a computing device in response to waking up the one or more sensors and the processor; establishing a communication with the computing device after initiating the advertisement; calibrating the one or more sensors in the insole after establishing the communication; and transmitting data from the one or more sensors to the computing device after calibrating the one or more sensors.

Example 12: The machine-readable storage media of example 11, having further machine-readable instructions stored thereon that, when executed, cause one or more machines to perform a further method comprising entering the low power mode if communication with the computing device is not established.

Example 13: The machine-readable storage media of example 11, wherein the one or more sensors comprises a pressure sensor coupled to a flexible printed circuit board, wherein the pressure sensor is to detect a point pressure on the insole.

Example 14: The machine-readable storage media of example 11, wherein the one or more sensors comprises a battery monitoring integrated circuit to provide a first data to calculate a charge level of a battery.

Example 15: The machine-readable storage media of example 11, wherein the one or more sensors comprises an inertial measurement unit to provide a second data to calculate parameters related to time, speed, and angles of the insole.

Example 16: The machine-readable storage media of example 11, wherein the one or more sensors comprises a barometric sensor to provide a third data to calculate height of the insole above a ground.

Example 17: A system comprising: a wireless communication interface in an insole; a processor which is communicatively coupled to a mobile device via the wireless communication interface; and a plurality of sensors coupled to the processor, wherein the mobile device is to receive a first data from the processor, wherein the first data is associated with the plurality of sensors, wherein the mobile device is to send a message to a medical professional or a medical system about the first data from the plurality of sensors, wherein the plurality of sensors include an inertial measurement unit to provide a second data to calculate parameters related to time, speed, and angles of the insole.

Example 18: The system of example 17, wherein the plurality of sensors includes a barometric sensor to provide a third data to calculate height of the insole above a ground.

Example 19: The system of example 17, wherein the plurality of sensors includes one or more pressure sensors to sense point pressure on the insole.

Example 20: The system of example 17, wherein the insole is a first insole, and wherein the mobile device is to establish a communication channel with a second insole separate from the first insole. While the disclosure has been described in conjunction with specific embodiments thereof, many alternatives, modifications and variations of such embodiments will be apparent to those of ordinary skill in the art in light of the foregoing description. The embodiments of the disclosure are intended to embrace all such alternatives, modifications, and variations as to fall within the broad scope of the appended claims.

What is claimed is:

1. A footwear insole apparatus comprising:
a flexible printed circuit board;
a relatively rigid printed circuit board coupled to the flexible printed circuit board;
a plurality of pressure sensors coupled to the flexible printed circuit board;
a processor coupled to the relatively rigid printed circuit board, wherein the processor is to receive sensor data from the plurality of pressure sensors;
a battery coupled to the relatively rigid printed circuit board, wherein the battery is used to power the plurality of pressure sensors and the processor;
a battery monitoring integrated circuit coupled to the processor via an I/O interface, wherein the battery monitoring integrated circuit is to provide a first data to calculate a charge level of the battery; and
an inertial measurement unit coupled to the processor via the I/O interface, wherein the inertial measurement unit is to provide a second data to calculate parameters related to time, speed, and angles of the footwear insole apparatus.

2. The footwear insole apparatus of claim 1, comprising a barometric sensor coupled to the processor via the I/O interface, wherein the barometric sensor is to provide a third data to calculate height of the footwear insole apparatus above a ground.

3. The footwear insole apparatus of claim 1, comprising an analog-to-digital converter (ADC) to receive an analog data from the plurality of pressure sensors and to generate a corresponding digital data for the processor.

4. The footwear insole apparatus of claim 1, comprising a voltage regulator to receive an input supply from the battery and to generate an output supply for the plurality of pressure sensors and the processor.

5. The footwear insole apparatus of claim 1, wherein the processor is to establish a Bluetooth connection with another device.

6. The footwear insole apparatus of claim 1, wherein the processor is to calibrate one or more sensors prior to transfer of data to another device.

7. The footwear insole apparatus of claim 1, wherein the processor is to enter a lower power mode if there is no pressure detected by the plurality of pressure sensors.

8. A footwear insole apparatus comprising:
a flexible printed circuit board;
a relatively rigid printed circuit board coupled to the flexible printed circuit board;
a plurality of pressure sensors coupled to the flexible printed circuit board;
a processor coupled to the relatively rigid printed circuit board, wherein the processor is to receive sensor data from the plurality of pressure sensors;
a battery coupled to the relatively rigid printed circuit board, wherein the battery is used to power the plurality of pressure sensors and the processor;
a battery monitoring integrated circuit coupled to the processor via an I/O interface, wherein the battery monitoring integrated circuit is to provide a first data to calculate a charge level of the battery; and
a barometric sensor coupled to the processor via the I/O interface, wherein the barometric sensor is to provide a third data to calculate height of the footwear insole apparatus above a ground.

9. The footwear insole apparatus of claim 8, comprising an inertial measurement unit coupled to the processor via the I/O interface, wherein the inertial measurement unit is to provide a second data to calculate parameters related to time, speed, and angles of the footwear insole apparatus.

10. The footwear insole apparatus of claim 8, comprising an analog-to-digital converter (ADC) to receive an analog data from the plurality of pressure sensors and to generate a corresponding digital data for the processor.

11. The footwear insole apparatus of claim 8, comprising a voltage regulator to receive an input supply from the battery and to generate an output supply for the plurality of pressure sensors and the processor.

12. The footwear insole apparatus of claim 8, wherein the processor is to establish a Bluetooth connection with another device.

13. The footwear insole apparatus of claim 8, wherein the processor is to calibrate one or more sensors prior to transfer of data to another device.

14. The footwear insole apparatus of claim 8, wherein the processor is to enter a lower power mode if there is no pressure detected by the plurality of pressure sensors.

\* \* \* \* \*